United States Patent
Vogt et al.

(10) Patent No.: US 6,913,764 B2
(45) Date of Patent: *Jul. 5, 2005

(54) ANTIBIOTIC(S) PREPARATION WITH RETARDING ACTIVE INGREDIENT RELEASE

(75) Inventors: Sebastian Vogt, Jena (DE); Matthias Schnabelrauch, Jena (DE); Klaus-Dieter Kühn, Marburg (DE)

(73) Assignee: Heraeus Kulzer GmbH & Co. KG, Hanau (DE)

(*) Notice: Subject to any disclaimer, the term of this patent is extended or adjusted under 35 U.S.C. 154(b) by 335 days.

This patent is subject to a terminal disclaimer.

(21) Appl. No.: 10/100,839

(22) Filed: Mar. 19, 2002

(65) Prior Publication Data

US 2002/0182251 A1 Dec. 5, 2002

(30) Foreign Application Priority Data

Mar. 22, 2001 (DE) .......................... 101 14 244

(51) Int. Cl.$^7$ .................................. A61K 2/02
(52) U.S. Cl. ................. 424/423; 424/426; 523/114; 523/115
(58) Field of Search ........................... 424/423, 426; 523/114, 115

(56) References Cited

U.S. PATENT DOCUMENTS

| | | | |
|---|---|---|---|
| 3,091,572 A | 5/1963 | Luedemann et al. | 167/65 |
| 3,536,759 A | 10/1970 | Jurado et al. | 260/559 |
| 3,882,858 A | 5/1975 | Klemm | 128/92 G |
| 4,059,684 A | 11/1977 | Gross et al. | 424/4 |
| 4,191,740 A | 3/1980 | Heusser et al. | 424/14 |
| 4,233,287 A | 11/1980 | Heusser et al. | 424/14 |
| 4,291,013 A | 9/1981 | Wahlig et al. | 424/16 |
| 4,617,293 A | 10/1986 | Wahlig et al. | 514/41 |
| 5,035,891 A | 7/1991 | Runkel et al. | 424/423 |
| 5,670,142 A | 9/1997 | Rubin | 414/78.05 |
| 5,709,875 A | 1/1998 | Lebugle et al. | 424/426 |
| 5,807,567 A | 9/1998 | Randolph et al. | 424/426 |
| 6,485,754 B1 * | 11/2002 | Wenz et al. | 424/602 |

FOREIGN PATENT DOCUMENTS

| | | | |
|---|---|---|---|
| BE | 821 600 | | 2/1975 |
| CN | 02108030.5 | * | 3/2001 |
| DE | 28 02 273 | | 7/1978 |
| DE | 32 48 328 A1 | | 6/1984 |
| EP | 0 052 916 | | 6/1982 |
| ES | 354173 | | 10/1970 |
| FR | 2 668 367 | | 4/1992 |
| GB | 1120992 | | 7/1968 |
| NL | 660 9490 | | 1/1967 |
| WO | 9527517 | | 10/1995 |

OTHER PUBLICATIONS

Abstract of WO 9527517 from EPO website database.
Abstract—ES 3309402; Conrado Folch Vazquez, "Tetracycline lauryl sulfate", Feb. 8, 1996.
Abstract—ES 322771; Conrado Folch Vazquez, "Tetracycline lauryl sulfate", Feb. 8, 1996.

* cited by examiner

*Primary Examiner*—Carlos A. Azpuru
(74) *Attorney, Agent, or Firm*—Norris McLaughlin & Marcus PA

(57) ABSTRACT

The present invention concerns an antibiotic/antibiotics preparation for resorbable and non-resorbable implants for human and veterinary medicine, for the treatment of local microbial infections in hard and soft tissue. The invented antibiotic/antibiotics preparation is a mixture consisting of at least one amphiphilic component of a representative of the alkyl sulfates, aryl sulfates, alkylaryl sulfates, cycloalkyl sulfates, alkylcycloalkyl sulfates, alkyl sulfamates, cycloalkyl sulfamates, alkylcycloalkyl sulfamates, aryl sulfamates, alkylaryl sulfamates, alkyl sulfonates, fatty acid-2-sulfonates, aryl sulfonates, alkylaryl sulfonates, cycloalkyl sulfonates, alkylcycloalkyl sulfonates, alkyl disulfates, cycloalkyl disulfates, alkyl disulfonates, cycloalkyl disulfonates, aryl disulfonates, alkylaryl disulfonates, aryl trisulfonates and alkylaryl trisulfonates as well as at least one antibiotic component from the group of aminoglycoside antibiotics, lincosamide antibiotics, 4-quinolone antibiotics and tetracycline antibiotics, and if need be at least one anhydrous organic auxiliary component and if need be at least one inorganic auxiliary component and if need be at least one biologically active component. The antibiotic/antibiotics preparation of the invention has a retarding active ingredient release.

15 Claims, No Drawings

ANTIBIOTIC(S) PREPARATION WITH RETARDING ACTIVE INGREDIENT RELEASE

The invention concerns an antibiotic/antibiotics composition and several uses.

The treatment of local microbial infections of hard and soft tissues in human and veterinary medicine requires high local antibiotics concentrations in the infected tissue region. It has been known for a long time that a systemic application of antibiotics is encumbered by a series of problems. With systemic use, it is often necessary to use very high antibiotics doses so that antimicrobially effective antibiotics concentrations are attained in the infected tissue. In this way, severe damage to the organism can occur in particular with aminoglucoside antibiotics and with tetracycline type antibiotics owing to their nephrotoxicity and ototoxicity. Therefore the idea of using antibiotics in locally applicable release systems or transferring them in suitable deposit forms suggested itself.

Deposit systems for delayed release of antibiotics for the treatment of local infections are the object of a great number of publications and patents. These can generally be classified according to two fundamental retarding mechanisms. The one action principle consists of the physiological fixation of the antibiotics through adsorption to a matrix or through inclusion in a non-resorbable or resorbable matrix. The second chemical delay principle consists of using sparingly soluble antibiotic salts which dissolve slowly following appropriate application in the human or animal organism while active ingredients are being released.

The physical fixation of antibiotics while using non-resorbable plastics was the subject of a series of patents of which here only a few are being presented as examples. Thus, Klemm (K. Klemm, Surgical synthetic resin material and method of treating osteomyelitis. May 13, 1975, U.S. Pat. No. 3,882,858) proposes treating osteomyelitis with plastic particles of polymethacrylate, polyacrylate or their copolymers which are impregnated with gentamicin (or: gentamycin) or other antibiotics. Klemm describes the use of septopal (K. Klemm: Septopal—a new way of local antibiotic therapy. In T. J. G. Van Rens, F. H. Kayser, (eds), Local Antibiotic Treatment in Osteomyelitis and Soft Tissue Infections, Excerpta Medica, Amsterdam (1981) 24–31; K. Klemm: Antibiotic beat chains. Clin. Orthop. Relat. Res. 295 (1993) 63–76). This involves commercially available gentamycin-releasing chains of polymethacrylate. Heuser and Dingeldein describe a composition based on antibiotics and polymethyl methacrylate or polyacrylate to which amino acids are added as additional components (D. Heuser, E. Dingeldein: Synthetic resin-base, antibiotic compounds containing amino acids. Apr. 4, 1980, U.S. Pat. No. 4,191, 740; D. Heuser, E. Dingeldein: Synthetic resin-base antibiotic compositions containing amino acids. Nov. 11, 1980, U.S. Pat. No. 4,233,287). Furthermore, antibiotics, especially aminoglycoside antibiotics, were incorporated into bone cements (A. Gross, R. Schaefer, S. Reiss: Bone cement compositions containing gentamycin. Nov. 22, 1977, U.S. Pat. No. 4,059,684; A. Welch: Antibiotics in acrylic bone cement. In vitro studies. J. Biomed. Mater. Res. 12 (1978) 679; R. A. Elson, A. E. Jephott, D. B. McGechie, D. Vereitas: Antibiotic-loaded acrylic cement. J. Bone Joint Surg. 59B (1977) 200–205.)

The physical fixation of antibiotics with the aid of resorbable plastics, especially of polyesters of α-hydroxy carboxylic acids, was likewise the object of a series of publications, of which only a few are reported here by way of example. Sampath et al. propose a gentamycin-releasing system consisting of poly-L-lactide and gentamycin which was manufactured by the pressing of poly-L-lactide/gentamycin microcapsules (S. S. Sampath, K. Garvin, D. H. Robinson: Preparation and characterization of biodegradable poly(-L-lactic acid) gentamycin delivery systems. Int. J. Pharmaceutics 78 (1992) 165–174). This system shows, as a function of the amount of gentamycin used, a considerable delay in active substance release. In a similar system, poly-D,L-lactide was used for manufacture of active ingredient-containing microspheres (R. Bodmeier, J. W. McGinty: The preparation and evaluation of drug-containing poly(D,L-lactide) microspheres formed by solvent evaporation method. Pharm. Res. 4 (1987) 465–471). Microparticles of poly lactide which are coated with collagen/gentamycin sulfate are likewise described by Fries and Schlapp (W. Fries, M. Schlapp: Advanced implants for local delivery of gentamicin. Sixth World Biomaterials Congress Transactions (2000) 1488). These coated microspheres showed but a very slight tendency to delay the release of gentamicin. Gentamicin-containing resorbable molded elements were proposed by Schmidt et. al. (C. Schmidt, R. Wenz, B. Nies, F. Moll: Antibiotic in vivo/in vitro release, histocompatibility and biodegradation of gentamicin implants based on lactic acid polymers and copolymers. J. Control. Release 37 (1995) 83–94). These elements were manufactured by the pressing of mixtures of gentamicin sulfate/poly-L-lactide, gentamicin sulfate/poly-D,L-lactide and gentamicin sulfate/poly-D,L-lactide-coglycolide. The deposit preparations released approximately ninety-percent of the antibiotic within twenty-four hours.

In addition to the physical fixation of antibiotics using plastics, numerous inorganic systems with retarding action were also described. Below only a few systems produced with calcium sulfate are reported by way of example. Thus a retarding system is described by Randolph et al., which is based upon the inclusion of active ingredients in a calcium sulfate matrix (D. A. Randolph, J. L. Negri, T. R. Devine, S. Gitelis: Calcium sulfate controlled release matrix. Sep. 15, 1998, U.S. Pat. No. 5,807,567). The manufacture of these calcium sulfate pellets takes place here proceeding from a mixture of α-calcium sulfate hemihydrate, β-calcium sulfate hemihydrate, an additive and water. Hardening takes place through the formation of calcium sulfate dihydrate. Turner et al. describe tablets of calcium sulfate which contain tobramycin and which are to be used to treat medullary defects (T. M. Turner, R. M. Urban, S. Gitelis, A. M. Lawrence-Smith, D. J. Hall: Delivery of tobramycin using calcium sulfate tablets to graft a large medullary defect: Local and systemic effects. Sixth World Biomaterials Congress Transactions (2000) 767). Similar release systems from calcium sulfate, but with amikacin sulfate, were likewise described (D. W. Petersen, W. O. Haggaard, L. H. Morris, K. C. Richelsoph, J. E. Parr: Elution of amikacin from calcium sulfate pellets: An in vitro study. Sixth World Biomaterials Congress Transactions (2000) 767).

Previously, sparingly soluble salts of aminoglycoside antibiotics, tetracycline antibiotics and lincosamide antibiotics received relatively little attention for the manufacture of deposit preparations. The formation of hard to dissolve salts or chelates of antibiotics of tetracycline type has been the general state of knowledge for years. Thus Folch Vazquez describes the manufacture of tetracycline dodecyl sulfate by the transformation of tetracycline hydrochloride with sodium dodecyl sulfate in water (C. Folch Vazquez: Tetracycline lauryl sulfate. Feb. 8, 1966, ES 3,309,402; C.

Folch Vazquez: Tetracycline derivatives. Jan. 9, 1967, NL 6609490). Alternatively, the manufacture can also take place proceeding from tetracycline and dodecyl sulfuric acid (C. Folch Vazquez: Tetracycline lauryl sulfate. Feb. 8, 1966, ES 322,771).

Furthermore, the use of tetracycline sulfamates for antibiotic therapy was proposed (A. Jurando, J. M. Puigmarti: Antibiotic tetracycline sulfamate and its derivatives. Oct. 27, 1970, U.S. Pat. No. 3,536,759; Anonymous: Antibiotic tetracycline alkylsulfamates. Oct. 16, 1969, ES 354,173; C. Ciuro, A. Jurado: Stability of a tetracycline derivative. Afinidad 28 (292) 1971, 1333–5). A series of sparingly soluble salts is also basically known in connection with aminoglucoside antibiotics. Thus, with gentamicin, the synthesis of hard to dissolve salts based on higher fatty acids, aryl alkyl carboxylic acids, alkyl sulfates and alkyl sulfonates was described (G. M. Luedemann, M. J. Weinstein: Gentamycin and method of production. Jul. 16, 1962, U.S. Pat. No. 3,091,572). Gentamicin salts of lauric acid, stearic acid, palmitic acid, oleic acid or phenyl butyric acid, naphthalene-1-carboxylic acid, lauryl sulfuric acid and dodecylbenzenesulfonic acid are examples of this. These salts prove disadvantageous in many ways because they represent wax-like (or: resinous), hydrophobic substances which impede a Galenic use. Despite this, fatty acid salts of gentamicin and etamycin were synthesized from the free base or from their salts in water at 50–80 C (H. Voege, P. Stadler, H. J. Zeiler, S. Samann, K. G. Metzger: Sparingly-soluble salts of aminoglycosides and formations containing them with inhibited substance release. Dec. 28, 1982, DE 3,248,328). These antibiotics-fatty acid salts are supposed to be suitable as injection preparations. The manufacture of gentamicin dodecyl sulfate and its use in salves (or: ointments), cremes was likewise described (C. Folch Vazquez: Gentamicin derivatives. Oct. 29, 1974, BE 821, 600). Even with lincosamide antibiotics, sparingly soluble salts, such as, for example, glindamycin palmitate, are known (M. Cimbollek, B. Nies, R. Wenz, J. Kreuter: Antibiotic-impregnated heart valve sewing rings for treatment and prophylaxis of bacterial endocarditis. Antimicrob. Agents Chemother. 40(6) (1996) 1432–1437). Sparingly soluble aminoglycoside flavonoid phosphates represent a more recent development (H. Wahlig, E. Dingeldein, R. Kirchlechner, D. Orth, W. Rogalski: Flavonoid phosphate salts of aminoglycoside antibiotics. Oct. 13, 1986, U.S. Pat. No. 4,617,293). The salts of phosphoric acid semi-esters of derivatives of hydroxy flavanes, hydroxy flavenes, hydroxy flavanones and hydroxy flavylium are described. The derivatives of flavanones and flavones are especially preferred. The sparingly soluble salts are supposed to be used as deposit preparations. Thus, for example, the salts in collagen shaped mass are utilized (H. Wahlig, E. Dingeldein, D. Braun: Medicinally useful, shaped mass of collagen resorbable in the body. Sep. 22, 1981, U.S. Pat. No. 4,291,013). Furthermore, even artificial heart valves are impregnated with these sparingly soluble gentamicin salts, gentamicin crobefate (M. Cimbollek, B. Nies, R. Wenz, J. Kreuter: Antibiotic-impregnated heart valve sewing rings for treatment and prophylaxis of bacterial endocarditis. Antimicrob. Agents Chemother. 40(6) (1996) 1432–1437). With this patent, it is particularly interesting that a mixture of easily soluble gentamicin sulfate and sparingly soluble gentamicin crobefate is used. The goal here was that, on the one hand, after introducing the heart valve rings into the organism or in a model fluid, a high initial gentamicin concentration is reached by the easily soluble gentamicin sulfate, and on the other hand through the relatively sparingly soluble gentamicin crobefate, a release of gentamicin over a longer period of time becomes possible. This means that the time-dependent release of gentamicin is controlled by the proportion of easily soluble gentamicin sulfate and sparingly soluble gentamicin crobefate. For a selective adjustment of the releasing behavior, it is therefore necessary to use the two gentamicin salts in defined proportions of ingredients into the Galenic formulations. This method of deposit formation through the combination of an easily soluble antibiotic salt with a sparingly soluble antibiotic salt presupposes the availability of a pure sparingly soluble salt form of an antibiotic.

In sum, it can be stated that the known antibiotic deposit systems with physically caused delay of the antibiotic release depend to a great extent on the composition of the matrix used. Furthermore, the production process of these antibiotic systems has considerable influence upon the releasing behavior. The disadvantage of systems with sparingly soluble antibiotic salts consists in that, for each antibiotic used, a special form of salt must be synthesized prior to manufacture of the deposit preparation.

Underlying the present invention is the problem of developing an antibiotic/antibiotics preparation with retarding active ingredient release as resorbable and also non-resorbable implants in the area of human and veterinary medicine for the treatment of local microbial infections in the bone and soft tissue which overcomes the disadvantages of the known retarding antibiotic formulations. Sought is an antibiotic/antibiotics preparation which enables a controlled antibiotics release in a period of time up to approximately three weeks. The mechanism of delayed active ingredient release should basically be independent of the supporting material and should not rest upon adsorption effects on surfaces of the supporting materials. Sought is an antibiotic/antibiotics preparation which can be processed into implants while retaining active ingredient retardation with resorbable as well as non-resorbable auxiliary materials of the most varied structure. Furthermore, the method of antibiotic/antibiotics preparation should not only be applicable for a specific antibiotic, but rather it should be suited for a series of antibiotics of similar structure.

This problem is solved in accordance with the invention as described herein.

Underlying the invention is the surprising finding that a mixture of at least one amphiphilic component of a representative of the alkyl sulfates, aryl sulfates, alkylaryl sulfates, cycloalkyl sulfates, alkylcycloalkyl sulfates, alkyl sulfamates, cycloalkyl sulfamates, alkylcycloalkyl sulfamates, aryl sulfamates, alkylaryl sulfamates, alkyl sulfonates, fatty acid 2-sulfonates, aryl sulfonates, alkylaryl sulfonates, cycloalkyl sulfonates, alkylcycloalkyl sulfonates, alkyl disulfates, cycloalkyl disulfates, alkyl disulfonates, cycloalkyl disulfonates, aryl disulfonates, alkylaryl disulfonates, aryl trisulfonates and alkylaryl trisulfonates as well as at least one antibiotic component from the group of aminoglycoside antibiotics, lincosamide antibiotics and tetracycline antibiotics shows a retarding active ingredient release over a period of time from several days up to several weeks in an aqueous medium.

The following embodiments have proven especially advantageous in practice.

First of all, it is advantageous that the antibiotics preparation has at least one anhydrous organic auxiliary component which has hydrolytically cleavable carboxylic acid ester compounds and/or hydrolytically cleavable carboxylic acid amide compounds and/or hydrolytically cleavable carboxylic acid anhydride compounds and/or hydrolytically cleavable phosphoric acid ester compounds and/or hydrolytically cleavable phosphoric acid amide compounds and/or enzymatically cleavable carboxylic acid ester compounds and/or enzymatically cleavable carboxylic acid amide compounds and/or enzymatically cleavable carboxylic acid anhydride compounds and/or enzymatically cleavable phosphoric acid ester compounds and/or enzymatically cleavable phosphoric acid amide compounds.

Furthermore, it is advantageous if the antibiotics preparation contains at least one inorganic auxiliary component from the calcium hydrogen phosphate, calcium hydrogen phosphate-dihydrate, hydroxyl apatite, fluorapatite, calcium polyphosphate, tricalcium phosphate, tetracalcium phosphate, calcium sulfate, calcium sulfate hemihydrate, calcium sulfate dihydrate, calcium lactate, sodium hydrogen carbonate, calcium carbonate, magnesium carbonate, calcium hydroxide, magnesium hydroxide, magnesium oxide group—the preceding substances in the form of a coarsely dispersed and/or highly dispersed powder—resorbable glasses, non-resorbable glasses, resorbable glass ceramics, non-resorbable glass ceramics, resorbable ceramics and non-resorbable ceramics.

Moreover, it is advantageous if the antibiotics preparation contains at least one biologically active auxiliary component from the penicillin antibiotics, the cephalosporin antibiotics, the 4-quinolone antibiotics and the macrolide antibiotics group, and optionally one or more representatives of the sulfonamide chemotherapeutic agents, analgesics and antiphlogistics agents group.

In accordance with the invention, it is advantageous if the amphiphilic components from the alkyl sulfates, aryl sulfates, alkylaryl sulfates, cycloalkyl sulfates and alkylcycloalkyl sulfates group as semi-esters are present in the form of a sodium salt and/or potassium salt and/or ammonium salt and/or trialkyl ammonium salt and/or dialkyl ammonium salt and/or monoalkyl ammonium salt and/or triaryl ammonium salt and/or diaryl ammonium salt and/or aryl ammonium salt and/or alkyldiaryl ammonium salt and/or dialkylaryl ammonium salt and/or tricycloalkyl ammonium salt and/or dicycloalkyl ammonium and/or monocycloalkyl ammonium salt and/or alkyldicycloalkyl ammonium salt and/or dialkylcycloalkyl ammonium salt and or in the form of an acid or an anhydride.

Furthermore, it is advantageous in accordance with the invention that the amphiphilic components from the alkyl sulfonates, fatty acid 2-sulfonates, alkyl sulfamates, cycloalkyl sulfamates, aryl sulfamates, alkylaryl sulfamates, aryl sulfonates, alkylaryl sulfonates, cycloalkyl sulfonates, alkylcycloalkyl sulfonates, alkyl disulfates, cycloalkyl disulfates, alkyl disulfonates, cycloalkyl disulfonates, aryl disulfonates, alkylaryl disulfonates, aryl trisulfonates and alkylaryl trisulfonates group are present in the form of a sodium salt and/or in the form of a potassium salt and/or in the form of an ammonium salt and/or in the form of a trialkyl ammonium salt and/or in the form of a dialkyl ammonium salt and/or in the form of a monoalkyl ammonium salt and/or in the form of a triaryl ammonium salt and/or in the form of a diaryl ammonium salt and/or in the form of an aryl ammonium salt and/or in the form of an alkyldiaryl ammonium salt and/or in the form of dialkylaryl ammonium salt and/or in the form of a tricyclealkyl ammonium salt and/or in the form of an alkyldicyclo ammonium salt and/or in the form of a monocycloalkyl ammonium salt and/or in the form of an alkyl dicycloalkyl ammonium salt and/or dialkylcycloalkyl ammonium salt and/or in the form of a sulfonic acid and/or in the form of a sulfonic acid anhydride.

In accordance with the invention, it is also advantageous for the antibiotic component to contain at least one amino group.

Furthermore, it is advantageous in accordance with the invention that at least one compound from the alkyl sulfates, cycloalkyl sulfates, cycloalkylalkyl sulfates, cycloalkyalkyl sulfates, aryl sulfates, alkylaryl sulfates, alkyl sulfamates, cycloalkyl sulfamates, alkylcycloalkyl sulfamates, aryl sulfamates, alkylaryl sulfamates, alkyl sulfonates, fatty acid 2-sulfonates, cycloalkyl sulfonates, cycloalkylalkyl sulfonates, aryl sulfonates and alkylaryl sulfonates with 6 to 30 carbon atoms in each case are preferred as amphiphilic components.

In accordance with the invention, aryl sulfates, alkylaryl sulfates, aryl sulfamates, alkylaryl sulfamates, aryl disulfonates, alkylaryl disulfonates, aryl trisulfonates and alkylaryl trisulfonates built up on the basis of monocyclic, dicyclic, tricyclic, tetracyclic, pentacyclic, hexacyclic, heptacyclic and octocyclic aromatic ring systems are preferred as amphiphilic components.

In accordance with the invention, cycloalkyl sulfates, alkylcycloalkyl sulfates, cycloalkyl sulfonates, alkylcycloalkyl sulfates, cycloalkyl sulfonates, alkylcycloalkyl sulfonates, built up on the basis of monocyclic, dicyclic, tricyclic, tetracyclic, pentacyclic, hexacyclic, heptacyclic and octocyclic saturated ring systems are preferred as amphiphilic components.

In accordance with the invention, sodium dodecyl sulfate, sodium tetradecyl sulfate, sodium hexadecyl sulfate, sodium octadecyl sulfate, sodium docosanyl sulfate, sodium dodecyl sulfonate, sodium tetradecyl sulfonate, sodium hexadecyl sulfonate, sodium octadecyl sulfonate, sodium dodecylbenzyl sulfonate and sodium cholesterol sulfate are especially preferred as amphiphilic components.

Furthermore, it is in accordance with the invention that especially allomycin, amicetin, amikacin, ampramycin, bekanamycin, betamicin, butirosin, destomycin, dibekacin, dihydrostreptomycin, flambamycin, fortimycin A, fortimycin B, framycetin, gentamicin, hikizimycin, homomycin, hybrimycin, hygromycin B, kanamycin, kasuhamycin, lividomycin, minosamycin, neomycin, netilmicin, paromomycin, parvulomycin, puromycin A, ribostamycin, rimocidin, ristosamine, ristomycin, sagamycin, sisomicin, sorbistin, spectionmycin, streptomycin, tobramycin, tunicamycin, vancomycin, verdamycin from the aminoglycoside antibiotics group are preferred as the antibiotic component.

In accordance with the invention, clindamycin and lincomycin are preferred as antibiotic components from the lincosamide antibiotics group.

Furthermore, ciprofloxacin or moxifloxacin are preferred as antibiotic components from the 4-quinolone antibiotics group.

It is in accordance with the invention that tetracycline, chlorotetracycline, oxytetracycline, demethyl chlorotetracycline, methacycline, doxycycline, rolitetracycline and minocycline are preferred as antibiotic components from the tetracycline antibiotics group.

It is also advantageous in accordance with the invention that the antibiotic component is present in the protonized salt form, whereby chloride ions, bromide ions, hydrogen sulfate ions, sulfate ions, dihydrogen sulfate ions, hydrogen phosphate ions, phosphate ions, acetate ions, succinate ions and lactate ions are preferred as counter-ions.

In accordance with the invention, it is furthermore preferred that 0.01 to 10 constituent parts by mole of the amphiphilic components are mixed with one molar part of the antibiotic components.

It is basic to the invention that through the ratio of the amount of amphiphilic components to the amount of antibiotic components, the proportion of the delay released antibiotic components to the overall amount of antibiotic components can be determined.

It is also advantageously in accordance with the invention that at least one compound from the oligoester and polyester of L-lactic and/or D-lactic acid and/or 2-hydroxy ethanoic acid and/or 2-hydroethoxyethanoic acid and/or 3-hydroxy butyric acid and/or 4-hydroxy butyric acid and/or 4-hydroxy hexanoic acid and 6-hydroxy hexanoic acid, and if need be co-oligo ester and/or co-polyester and if need be ter-oligoester and/or ter-polyester of hydroxy carboxylic acid are used as anhydrous, organic auxiliary components.

It is in accordance with the invention that oligoamides and/or polyamides are used as anhydrous organic auxiliary components which contain amino acids as components.

In accordance with the invention, the amino acids glycine and/or L-alanine and/or D-alanine and/or L-valine and/or D-valine and/or L-threonine and/or D-threonine and/or L-aspartic acid and/or D-aspartic acid and/or L-asparagine and/or D-asparagine and/or L-glutamic acid and/or D-glutamic acid and/or L-glutamine and/or D-glutamine and/or L-ornithine and/or D-ornithine and/or L-lysine and/or D-lysine and/or 3-amino propanoic acid and/or R-2-amino butyric acid and S-2-amino butyric acid and/or 3-amino butyric acid and/or 4-amino butyric acid and/or R-2-amino pentanoic acid and/or S-2-amino butyric acid and/or 3-amino pentanoic acid and/or 4-amino pentanoic acid and/or 5-amino pentanoic acid and/or R-2-amino hexanoic acid and/or amino S-2-amino hexanoic acid and/or 3-amino hexanoic acid and/or 4-amino hexanoic acid and/or 5-amino hexanoic acid and/or 6-amino hexanoic acid and/or R-2-amino heptanoic acid and/or S-2-heptanoic acid and/or 3-amino-heptanoic acid and/or 4-amino heptanoic acid and/or 5-amino heptanoic acid and/or 6-amino-heptanoic acid and/or 7-heptanoic acid and/or R-2-amino octanoic acid and/or S-[2]-octanoic acid and/or 3-amino octanoic acid and/or 4-amino octanoic acid and/or 5-amino octanoic acid and/or 6-amino octanoic acid and/or 7-amino octanoic acid and/or 8-amino octanoic acid and/or R-2-amino nonanoic acid and/or S-2-amino nonanoic acid and/or 3-amino nonanoic acid and/or 4-amino nonanoic acid and/or 5-amino nonanoic acid and/or 6 amino nonanoic acid and/or 7-amino nonanoic acid and/or 8-amino nonanoic acid and/or 9-amino nonanoic acid and/or R-2-amino decanoic acid and/or S-2-amino decanoic acid and/or 3-amino decanoic acid and/or 4-amino decanoic acid and/or 5-amino decanoic acid and/or 6-amino decanoic acid and/or 7-amino decanoic acid and/or 8-amino decanoic acid and/or 9-amino decanoic acid and/or 10-amino decanoic acid and/or 11-amino undecanoic acid and/or L-phenylalanine and/or D-phenylalanine and/or L-tyrosine and/or D-tyrosine and/or L-histidine and/or D-histidine and/or L-tryptophan and/or D-tryptophan are used as building blocks of the oligoamides and polyamides.

In accordance with the invention, preferably aliphatic alcohols with a number from 12 to 30 carbon atoms are used as anhydrous, organic auxiliary components.

It is furthermore in accordance with the invention that preferably fatty acids with a number from 12 to 30 carbon atoms are used as anhydrous auxiliary components.

It is also in accordance with the invention that glycerin tri-fatty acid esters, glycerin di-fatty acid esters and glycerin mono-fatty acid esters are preferred as anhydrous, organic auxiliary components, whereby the fatty acid radicals contain 14 to 22 carbon atoms in each case.

It is in accordance with the invention that n-alkanes and iso-alkanes with 6 to 30 carbon atoms are preferred as anhydrous, organic auxiliary components.

In accordance with the invention, that poly ethylene glycol and/or poly propylene glycol with molar masses in the range from 200 to 35,000 are preferred as anhydrous, organic auxiliary components.

In accordance with the invention, polyethylene oxide and polypropylene oxide with molar masses in the 35,000 to 1,000,000 range are preferred as organic auxiliary components.

In accordance with the invention, at least one compound of the gelatine, collagen, cellulose, carboxy methyl cellulose, methyl cellulose, ethyl cellulose, hydroxy ethyl cellulose, propyl cellulose, hydroxy propylcellulose, butyl cellulose, starch, carboxy methyl starch, methyl starch, ethyl starch, hydroxy ethyl starch, propyl starch, hydroxy propyl starch, butyl starch, chitin, carboxymethyl chitin, chitosan, carboxymethyl chitosan, glycogen, carboxymethyl glycogen, alginic acid, alginic acid methyl ester, hyaluronic acid, carboxymethyl hyaluronic acid, cellulose acetate, cellulose proprionate, cellulose butyrate, cellulose phthalate, cellulose sulfate, cellulose phosphate, starch acetate, starch proprionate, starch butyrate, starch phthalate, starch sulfate, starch phosphate, oxidized cellulose, oxidized starch, pullulan, araban, xanthan, guar gum group is preferred as anhydrous, organic auxiliary components.

In accordance with the invention, anhydrous, organic auxiliary components such as carnauba wax, beeswax, benzoin resin, collophonium and copal resin are preferred.

In accordance with the invention, at least one compound of the polyethylene, polypropylene, polybutadiene, polyisoprene, polychlorbutadiene, polymethyl methacrylate, poly-2-hydroxymethyl methacrylate, polymethacrylate, polystyrene, polyvinyl acetate, polyvinyl alcohol, polyvinyl chloride, polyvinylidene chloride, polyvinyl fluoride, polyvinyl pyrrolidone, polytetrafluoroethylene, polycarbonate, polysulfone, polysiloxane and mixtures of these polymers is preferred as anhydrous organic auxiliary components.

In accordance with the invention, at least one compound from the acrylic acid ester, acrylic acid amide, methacrylic acid ester, methacrylic acid amide, itaconic acid ester, maleimide group and mixtures of them are preferred as anhydrous organic auxiliary components.

In accordance with the invention, it is advantageous that the anhydrous, organic auxiliary component is present in a solid and/or liquid state.

It is also in accordance with the invention that aryl sulfate, aryl sulfonate, aryl sulfamate and alkylaryl sulfonate are if need be components of a non-cross-linked polymer and/or a cross-linked polymer, whereby polymers from the polystyrene, polymethacrylate, polyacrylates, polyamides or polycarbonates group and/or their co-polymers and/or their ter-polymers are preferred.

In addition, it is of advantage if the antibiotics composition is present as molded elements, granulates, powders, foils, tubes, shaped masses or threads manufactured by pressing and/or extrusion and/or grinding and/or calendering and/or casting and/or spinning and/or sintering.

Above and beyond this, it is advantageous if the salt-like component and the antibiotic component are suspended in the anhydrous, organic auxiliary component and form an injectable suspension.

Finally, it is of particular significance that the antibiotics preparation of the invention can be used as implants in the form of molded elements, granulates, powders, tubes, foils, shaped masses and threads, especially if these are plastically moldable and modelable. This also applies for possible coatings to resorbable porous glasses, to non-resorbable glasses, resorbable porous glass ceramics, non-resorbable glass ceramics, resorbable porous ceramics and non-resorbable porous ceramics including resorbable plastic implants, non-resorbable plastic implants and metal implants.

Through the proportion of the molar amount of amphiphilic components to the molar amount of the antibiotic component, the proportion of delay-released antibiotic component in the overall amount of the antibiotic component can be determined.

The object of the present invention is to be explained in greater detail on the basis of the following examples 1–6.

Manufacture of the antibiotic/antibiotics preparation.

EXAMPLE 1

A mixture of 51 mg of gentamicin sulfate (700 U/mg, Fluka), 51 mg of sodium dodecyl sulfate (Aldrich), 280 mg poly L-lactide (molar mass~10,000 gmol-1) and 1118 mg calcium hydrogen phosphate (Fluka) is prepared. In each case, 200 mg of this mixture are pressed with a press at a pressure of 5 tons inside of two minutes to disk-like molded elements with a diameter of 13 mm.

EXAMPLE 2

A mixture of 51 mg of gentamicin sulfate (700 U/mg, Fluka), 51 mg of sodium dodecyl sulfate (Aldrich), 280 mg of poly L-lactide (molar mass~10,000 gmol-1) and 1118 mg of calcium hydrogen phosphate-dihydrate (Fluka) is prepared. In each case, 200 mg of this mixture are pressed with a pressure under a pressure of 5 tons inside two minutes to disk-like molded bodies with a diameter of 13 mm.

EXAMPLE 3

A mixture of 51 mg of gentamicin sulfate (700 U/mg), 51 mg of sodium dodecyl sulfate (Aldrich), 280 mg of poly-L-lactide (molar mass~10,000 gmol-1) and 1118 mg of calcium sulfate dihydrate (Fluka) is prepared. In each case, 200 mg of this mixture are pressed with a press at a pressure of 5 tons inside of two minutes to disk-like molded elements with a diameter of 13 mm.

EXAMPLE 4

A mixture of 51 mg gentamicin sulfate (700 U/mg, Fluka), 51 mg of sodium dodecyl sulfate (Aldrich), 280 mg of carnauba wax (Aldrich) and 1118 mg of calcium hydrogen phosphate (Fluka) is prepared. In each case, 200 mg of this mixture are pressed with a press at a pressure of 5 tons inside of two minutes into disk-like molded elements with a diameter of 13 mm.

EXAMPLE 5

A mixture of 51 mg of gentamicin sulfate (700 U/mg, Fluka), 51 mg of sodium dodecyl sulfonate (Aldrich), 280 mg of poly L-lactide (molar mass~10,000 gmol-1) and 1118 mg of calcium hydrogen phosphate (Fluka) is prepared. In each case, 200 mg of this mixture are pressed with a pressure under a pressure of 5 tons inside two minutes to disk-like molded bodies with a diameter of 13 mm.

EXAMPLE 6

A mixture of 51 mg of gentamicin sulfate (700 U/mg, Fluka), 51 mg of sodium dodecyl benzyl sulfonate (Aldrich), 280 mg of poly L-lactide (molar mass~10,000 gmol-1) and 1118 mg of calcium hydrogen phosphate (Fluka) is prepared. In each case, 200 mg of this mixture are pressed with a pressure under a pressure of 5 tons inside two minutes to disk-like molded bodies with a diameter of 13 mm.

Antibiotic Release Experiments

The molded elements prepared in examples 1–6 were introduced into a physiological saline solution and stored in this at 37 C over a period of four weeks in order to determine the retarded antibiotic release. Sampling took place after 1, 3, 6, 9, 12, 14 and 21 days of storage time. The antibiotics value determination was conducted with an agar diffusion test using Bacillus subtilis ATCC 6633 as a test germ (for results, see Table 1).

TABLE 1

Cumulative gentamicin release from sample elements from examples 1–6 as a function of storage time in physiological saline solution at 37° C.

| Examples | Cumulative gentamicin release (Ma %) Storage time (d) | | | | | | |
|---|---|---|---|---|---|---|---|
| | 1 | 3 | 6 | 9 | 12 | 14 | 21 | 51 |
| 1 | 32 | 54 | 67 | 72 | 77 | 83 | 94 | 100 |
| 2 | 45 | 54 | 63 | 71 | 77 | 82 | 88 | 100 |
| 3 | 48 | 57 | 64 | 78 | 84 | 91 | 100 | 100 |
| 4 | 43 | 51 | 58 | 71 | 81 | 93 | 100 | 100 |
| 5 | 50 | 69 | 85 | 95 | 99 | 100 | 100 | 100 |
| 6 | 77 | 82 | 86 | 90 | 94 | 97 | 100 | 100 |

What is claimed is:

1. Antibiotic/antibiotics preparation, comprising a mixture of:
    a) at least one amphiphilic component selected from the group of alkyl sulfates, aryl sulfates, alkylaryl sulfates, cycloalkyl sulfates, alkylcycloalkyl sulfates, alkyl sulfamates, cycloalkyl sulfamates, alkylcycloalkyl sulfamates, aryl sulfamates, alkylaryl sulfamates, alkyl sulfonates, fatty acid-2-sulfonates, aryl sulfonates, alkylaryl sulfonates, cycloalkyl sulfonates, alkylcycloalkyl sulfonates, alkyl disulfates, cycloalkyl disulfates, alkyl disulfonates, cycloalkyl disulfonates, aryl disulfonates, alkylaryl disulfonates, aryl trisulfonates and alkylaryl trisulfonates and b) at least one antibiotic component selected from the group of aminoglycoside antibiotics, lincosamide antibiotics, 4-quinolone antibiotics and tetracycline antibiotics;
    b) at least one anhydrous, organic auxiliary component which has hydrolytically cleavable carboxylic acid ester compounds and/or hydrolytically cleavable carboxylic acid amide compounds and/or hydrolytically cleavable carboxylic acid anhydride compounds and/or hydrolytically cleavable phosphoric acid ester compounds and/or hydrolytically cleavable phosphoric acid amide compounds and/or enzymatically cleavable carboxylic acid ester compounds and/or enzymatically cleavable carboxylic acid amide compounds and/or enzymatically cleavable carboxylic acid anhydride compounds and/or enzymatically cleavable phosphoric acid compounds and/or enzymatically cleavable phosphoric acid amide compounds; and
    c) at least one inorganic auxiliary component selected from the group of calcium hydrogen phosphate, calcium hydrogen phosphate-dihydrate, hydroxyl apatite, fluorapatite, calcium polyphosphate, tricalcium phosphate, tetracalcium phosphate, calcium sulfate, calcium sulfate hemihydrate, calcium sulfate dihydrate, calcium lactate, sodium hydrogen carbonate, calcium carbonate, magnesium carbonate, calcium hydroxide, magnesium hydroxide, magnesium oxide group—the preceding substances in the form of a coarsely dispersed and/or highly dispersed powder—resorbable glasses, non-resorbable glasses, resorbable glass ceramics, non-resorbable glass ceramics, resorbable ceramics and non-resorbable ceramics.

2. Antibiotic/antibiotics preparation according to claim 1, wherein this preparation contains (a) at least one biologically active auxiliary component selected from the group consisting of penicillin antibiotics, cephalosporin antibiotics, 4-quinolone antibiotics and the macrolide antibiotics and (b) one or more representatives selected from the group consisting of the sulfonamide chemotherapeutic agents, analgesics and anti-phlogistics agents.

3. Antibiotic/antibiotics preparation according to claim 1, wherein the antibiotic component contains at least one amino group.

4. Antibiotic/antibiotics preparation according to claim 1, wherein the antibiotic component is present in a protonized salt form, whereby chloride ions, bromide ions, hydrogen sulfate ions, sulfate ions, dihydrogen phosphate ions, hydrogen phosphate ions, phosphate ions, acetate ions, succinate ions and lactate ions are used as counter-ions.

5. Antibiotic/antibiotics preparation according to claim 1, wherein this preparation is present as molded elements, granulates, foils, powders, tubes, shaped masses or threads manufactured by pressing and/or extrusion and/or grinding and/or calendering and/or casting and/or spinning and/or sintering.

6. Antibiotic/antibiotics preparation according to claim 1, wherein the amphiphilic component and the antibiotic component are suspended in the anhydrous, organic auxiliary component and form an injectable suspension.

7. An injectable suspension comprising an antibiotic/antibiotics preparation according to claim 1.

8. An implant comprising an antibiotic/antibiotics preparation according to claim 1.

9. The implant according to claim 8, which is in the form of molded elements, granulates, powders, tubes, foils, shaped masses or threads.

10. The implant according to claim 9, wherein the molded elements, granulates, powders, tubes, foils, shaped masses or threads are plastically moldable or modelable.

11. A method of preparing an implant comprising coating an antibiotic/antibiotics preparation according to claim 1 on a material selected from resorbable porous glasses, non-resorbable glasses, resorbable porous glass ceramics, non-resorbable porous glass ceramics, resorbable porous ceramics and non-resorbable porous ceramics.

12. A method of preparing an implant comprising coating an antibiotic/antibiotics preparation according to claim 1 on a material selected from resorbable plastic implants, non-resorbable plastic implants and metal implants.

13. A method of obtaining a delayed release of antibiotic/antibiotics, comprising providing an antibiotic/antibiotics preparation according to claim 1, whereby the proportion of delay released antibiotic component to the overall amount of antibiotic component in said antibiotic/antibiotics preparation is determined by the ratio of the molar amount of an amphiphilic component in said antibiotic/antibiotics preparation to the molar amount of said antibiotic component.

14. A method of preparing an implant comprising providing an implant in the form of at least one of molded elements, granulates, powders, tubes, foils, shaped masses and threads, and providing an antibiotic/antibiotics preparation according to claim 1, and coating the implant with said antibiotic/antibiotics preparation by a process comprising one or more of pressing, immersion, spraying, calendaring, extrusion, sintering and melting.

15. A method of treating a microbial infection in a human or animal comprising treating said human or animal with an antibiotic/antibiotics preparation according to claim 1.

* * * * *